United States Patent [19]

Vasilevskis

[11] 4,130,712

[45] Dec. 19, 1978

[54] SYNTHESIS OF BIOTIN

[75] Inventor: Janis Vasilevskis, West Caldwell, N.J.

[73] Assignee: Hoffmann-La Roche Inc., Nutley, N.J.

[21] Appl. No.: 807,760

[22] Filed: Jun. 17, 1977

Related U.S. Application Data

[63] Continuation-in-part of Ser. No. 704,157, Jul. 12, 1976, abandoned.

[51] Int. Cl.$^2$ ............................................. C07D 495/04
[52] U.S. Cl. .................................. 548/303; 424/273 R
[58] Field of Search ........................................... 548/303

[56] References Cited

U.S. PATENT DOCUMENTS

| | | | |
|---|---|---|---|
| 2,487,051 | 11/1949 | Mozingo | 548/303 |
| 2,502,422 | 4/1950 | Cheney | 548/303 |
| 4,054,740 | 10/1977 | Field | 548/303 |

OTHER PUBLICATIONS

Wagner et al. Synthetic Organic Chem. p. 567, John Wiley & Sons, N.Y. 1953.

Allinger et al., Organic Chem., Worth, N.Y. 1972. pp. 532-533.

*Primary Examiner*—Natalie Trousof
*Assistant Examiner*—Jane T. Fan
*Attorney, Agent, or Firm*—Jon S. Saxe; Bernard S. Leon; George W. Johnston

[57] ABSTRACT

A procedure for the synthesis of biotin is disclosed whereby unsaturated diacylated biotin precursors are catalytically hydrogenated with the substantial absence of sulfur poisoning. The hydrogenation procedure disclosed herein results in optically pure biotin.

7 Claims, No Drawings

4,130,712

SYNTHESIS OF BIOTIN

CROSS-REFERENCE TO RELATED APPLICATIONS

This application is a continuation-in-part of U.S. patent application Ser. No. 704,157 filed July 12, 1976, now abandoned.

BACKGROUND OF THE INVENTION

Biotin (vitamin H) plays an essential nutritional role in various $CO_2$ fixation reactions. Additionally, biotin serves an important function as a growth factor in poultry. Its relative unavailability from natural sources has spurred interest in synthetic approaches. Many syntheses of biotin are known in the literature. One common problem shared by all of these syntheses is that at some point therein the need for reduction of an unsaturated precursor, usually a thiophene precursor, arises. Because of the presence of the sulfur moiety in the thiophene ring, catalyst poisoning, where catalytic reduction means are employed, presents a formidable problem. Many solutions have been proposed. See for instance Taguchi et al. *Chemistry Letters*, 1974 (pages 729–730); Mozingo et al. U.S. Pat. No. 2,487,051 and Enoki et al. U.S. Pat. No. 3,905,995. However, problems such as sulfur loss, with a concomitant decrease in biotin yield, and catalyst poisoning persist.

The instant invention provides a means whereby the necessary biotin precursor hydrogenation can be accomplished without the problems realized heretofore by diacylating these precurosrs prior to hydrogenation.

SUMMARY OF THE INVENTION

In accordance with the instant invention, biotin may be prepared by way of the following scheme:

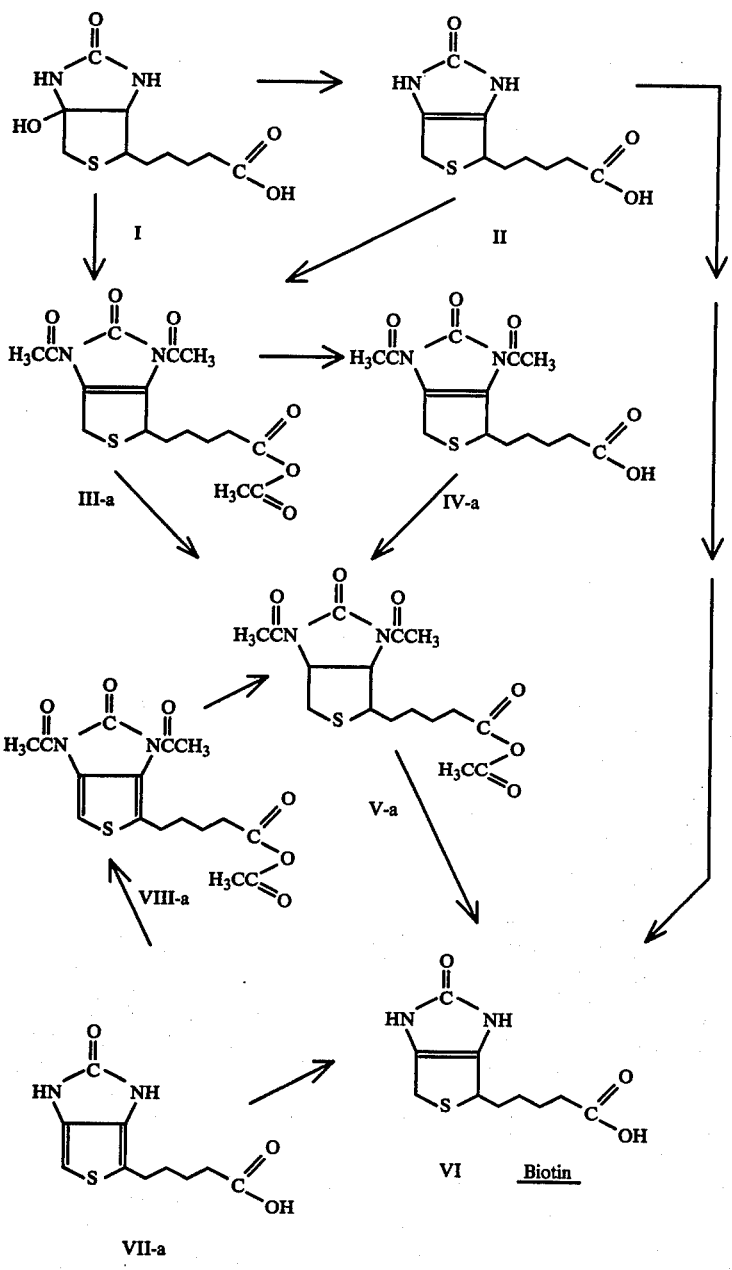

3

In the foregoing scheme the reaction sequences involving compounds I through VI illustrate a preferred biotin syntheses. The reaction sequences illustrated by compounds VII-a-VIII-a-V-a-VI represent an alternative route to biotin where the starting material is 2,3-dihydro-2-oxo-1H-thieno[3,4-d]imidazole-4-pentanoic acid (aromatic biotin).

DESCRIPTION OF THE INVENTION

As used herein the term "lower alkyl" denotes straight or branched alkyl groups having from one to six carbon atoms. Such lower alkyl groups are methyl, ethyl, propyl, etc. The term "lower acyl" denotes acyl groups having from 1-6 carbon atoms. Typical lower acyl groups are acetyl, propionyl, butyryl, etc. The term "lower alkanoic acid" as used herein denotes an alkanoic acid having from 1-6 carbon atoms. The term "halogen" or "halide" as used herein refers to bromine, chlorine, iodine, and fluorine. The term "alkali metal" as used herein refers to sodium, potassium and lithium. The term "alkaline earth metal" as used herein refers to calcium, barium and magnesium.

Biotin is prepared in accordance with this invention by first dehydrating a compound of the formula

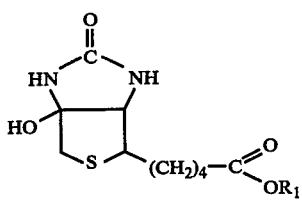

wherein $R_1$ is hydrogen, lower alkyl or lower acyl to form a compound of the formula

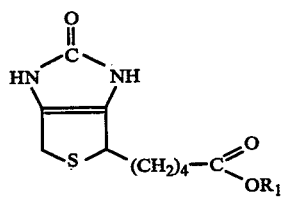

wherein $R_1$ is as above.

The preparation of compounds I and II is disclosed and claimed in a patent application of Field, Ser. No. 610,707 filed Sept. 5, 1975, now U.S. Pat. No. 4,054,740, which is a c-i-p of Ser. No. 536,139 filed Dec. 24, 1974, now abandoned, the disclosures of which are incorporated herein by reference. Succinctly, the conversion of compound I to compound II is accomplished by treating compound I under acid conditions in the presence of dehydrating agents such as $P_2O_5$, $SOCl_2$, $H_2SO_4$, $H_3PO_4$, activated alumina, and a lower alkanoic acid ahydride, preferably acetic anhydride, at a temperature ranging from 0° C. to 75° C. The reaction is generally carried out at atmospheric pressure, preferably in the presence of an inert atmosphere, i.e., nitrogen.

Compound II is then converted to a compound of the formula

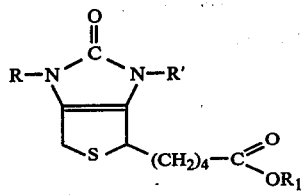

wherein R and R' are lower acyl and $R_1$ is as defined above.

Compound III is novel and provides an additional aspect of the invention.

Compound III is prepared by heating a solution of compound II in a lower alkanoic acid anhydride, preferably acetic anhydride, at a temperature of from about 80° C. to the boiling point of the solvent, preferably at about 115° C.

Compound III may be prepared directly from compound I by employing the same conditions for the preparation of compound III from compound II. The direct preparation of compound III from compound I has obvious advantages in that a preparative step is eliminated. However, compound III is recovered as an oil, creating workup problems. It can readily be seen that the preparation of compound III from compound II represents a viable alternative. The reaction may, if desired, be carried out in a lower alkanoic acid-acid anhydride cosolvent system. However, a lower alkanoic acid anhydride solvent is preferred.

When compound III has been obtained as the anhydride, it is then transformed to a compound of the formula

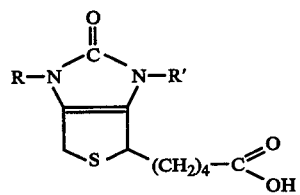

wherein R and R' are as defined above.

The transformation of compound III to compound IV is accomplished by conventional acid hydrolysis techniques. Lower alkanoic acids, preferably acetic acid, are employed in the hydrolysis. Compound IV is also novel and forms an additional aspect of this invention.

Compounds III may also be obtained as the corresponding ester by treating compound I or II with a lower alkanol in the presence of an acid catalyst followed by acylation. The resulting compound IIIb is reduced as described below. Compound IIIb is preferably obtained as the methyl ester. In carrying out the preparation of compound IIIb typical acid catalysts employed are $H_2SO_4$, HCl, p-toluenesulfonic acid, $H_3PO_4$ and the like. The specific ester obtained will be governed by the lower alkanol employed, e.g., methyl alcohol will yield the methyl ester and so on.

Compound III or IV is then transformed to a compound of the formula

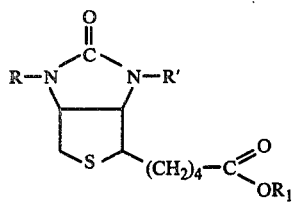

wherein R, R' and R₁ are as previously defined by either catalytic hydrogenation or chemical reduction.

The catalysts employed in the transformation of compounds III or IV to compound V may be selected from Raney nickel, Raney cobalt, finely divided platinum, platinum on a carbon support, platinum oxide, palladium on a carbon support, salts of palladium and complexes thereof. Typical palladium compounds that may be used are Pd(OH)₂/C, Pd/C, Pd(S)/C, the dibenzylidene acetone complex of palladium, π-allyl complexes of palladium halides, preferably chlorides, dimethylglyoxime complex of palladium, 2,6-diaminopyridine complex of palladium. As previously stated, desulfurization, with concomitant decreased product yield, is a problem when attempting to reduce unsaturated sulfur containing compounds. It has been found that diacylation, preferably diacetylation, of unsaturated biotin precursors minimizes desulfurization problems. This is all the more striking in view of the fact that Pd/S type catalysts may be employed.

The catalytic reduction of compound III or IV to compound V may be accomplished by treating either compound with any of the above-mentioned catalysts under solvent conditions, at a concentration of from about 0.1 weight % to 10 weight % of compound III or IV to solvent. The solvents generally employed are water, lower alkanols, preferably methanol, lower alkanoic acid or their anhydrides, preferably acetic acid or acetic anhydride. The reduction temperature may vary from ambient to about 115° C., with a temperature of about 85° C. being preferred. The reaction can be carried out at lower or higher temperatures but the former may result in slow reaction times while the latter may lead to decomposition or highly discolored product. The pressure may vary from 60 psig to about 2000 psig.

A distinct advantage of this hydrogenation procedure is that the catalysts, particularly the palladium compounds can be reused. Some of the palladium compounds can be reused up to 20 times with little or no loss in activity. The economics of such a feature is immediately apparent. The seemingly greater activity of the palladium salts is believed to be due, without being bound to any particular theory, to the formation of fine Pd crystals.

Platinum on carbon and platinum oxide have also been found to be effective hydrogenation catalysts. Particularly preferred is platinum oxide.

The catalytic reduction of compound III or IV gives a product where the desired all-cis isomer predominates over the epi by ~20/1. If one has optical activity at ring position 2, one can obtain ~95% isomerically pure d- or l-biotin.

Compounds III or IV may be chemically reduced by employing a hydride reducing agent in strong acid. The hydride reducing agent that is used must be one that will reduce the double bond but not hydrolyze the substituents R and R'. Typical hydrides that may be used are triethylaminoborane, trichlorosilane and trialkylsilanes, preferably triethylsilane. The strong acids that are used may generally be selected from HCl, H₃PO₄, CX₃COOH, HCX₂COOH or H₂CXCOOH where X is halogen, preferably chlorine or fluorine.

It has been found that this type of chemical reduction of either mono or di-acylated compound III or IV improves the ratio of cis to epi-biotin obtained as compared to from compound II. When either of compounds III or IV is di-acylated, the ratio of cis to epi-biotin is greater than 6/1.

Compound V may be formed directly from compound III by employing the identical conditions for the transformation of compound IV to compound V. This alternative is viable in that it eliminates a process step.

Compound VI, biotin, is then obtained by basic hydrolysis of compound V. The hydrolysis is carried out under conventional procedures employing aqueous or alcoholic ammonia, alkali metal carbonates or hydroxides. Sodium is the preferred alkaline metal. Alkaline earth metal bases may also be employed. The hydrolysis is preferably carried out at a temperature ranging from room temperature to the boiling point of the solvent.

Another of the advantages of the foregoing reaction sequence is that, depending upon the disposition of the hydrogens at the 2, 3, and 4 positions of the thieno ring, either d, or l biotin will be obtained. Optically pure d or l biotin is obtainable if there is optical activity at the 2-position of the thieno ring, i.e., where the side chain is present. It has consistently been noted that the reduction product, i.e., compound V, is exclusively all cis and reflects the initial isomeric content of compounds I and II. Succinctly, this reaction proceeds with no racemization.

A still further aspect of this invention is the obtention of biotin by the treatment of a compound of the formula

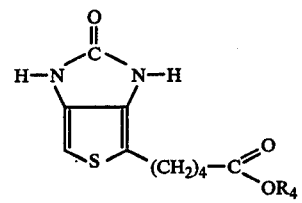

wherein R₄ is hydrogen, lower alkyl or lower acyl with a lower acyl anhydride, in the same manner and under the same conditions as the transformation of compound II to compound III, to form a compound of the formula

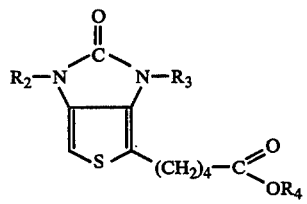

wherein R₂ and R₃ are lower acyl and R₄ is as defined above.

Compound VIII is then transformed to compound V according to essentially the same procedure as that employed for the catalytic reduction of compound III to compound V. In this transformation the reaction pressure must be at least 550 psi. Compound V may then be converted to biotin as hereinbefore described. The biotin product obtained in accordance with this procedure is an all cis d,l mixture requiring a subsequent resolution step to obtain the active all cis d-biotin.

The following non-limiting examples serve to illustrate the instant invention. All temperatures are in degrees Centigrade.

EXAMPLE 1

1,3-Diacetyl-2,3,4,6-tetrahydro-2-oxo-1H-thieno[3,4-d]imidazole-4-pentanoic acid anhydride [N,N-diacetyldehydro-biotin acetyl anhydride]

20.0 g. of 6a-hydroxy-2-oxo-hexahydro-1H-thieno[3,4-d]imidazole-4-pentanoic acid (hydroxybiotin) (77 mmol) rich in the 1-isomer was added to 130 ml. of distilled acetic anhydride. The solution was heated under an inert atmosphere at 115° C. for 4.5 hours. The resulting dark brown solution was stripped of acetic anhydride yielding a dark oil. The mixture was restripped by washing three times with a chloroform/toluene mixture yielding 29.92 g. of brown crystalline product. Some solvent is still trapped in the product. The crude product is redissolved in 65 ml. of chloroform and is placed on a 110 ml. silica gel plug. Elution is carried out with 500 ml. chloroform. Stripping yielded 22.45 g. of cream colored crystalline product, 1,3-diacetyl-2,3,4,6-tetrahydro-2-oxo-thieno[3,4-d]imidazole-4-pentanoic acid (87% yield).

EXAMPLE 2

1,3-Diacetyl-2,3,4,6-tetrahydro-2-oxo-1H-thieno[3,4-d]imidazole-4-pentanoic acid anhydride [N,N-diacetyldehydro-biotin acetyl anhydride]

45.60 g. (190 mmole) of dehydrobiotin rich in the d-isomer was placed in 750 ml. of methanol. The mixture was brought to reflux and all solids dissolved. 5.0 g. of Norit A charcoal was added and the solution was refluxed for 1½ hours. The carbon was filtered while keeping the solution hot. Crystallization began immediately and is completed at ~0° C. The first crop yielded 41.75 g. of dehydrobiotin. Stripping of the solvent to 100 ml. yielded a second crop of 1.36 g. of colorless crystalline dehydrobiotin for a total yield of 43.11 g. (95%) of purified dehydrobiotin.

The recrystallized dehydrobiotin was dissolved in 260 ml. of distilled acetic anhydride. The solution was heated at 115° C. for 4.5 hours. The orange reaction mixture was stripped of solvent under vacuum. The product was restripped twice from 200 ml. toluene leaving a tan crystalline material. 60.7 g. represents quantitative yields since dehydrobiotin tends to entrap solvent and the product is slightly hydrolyzed.

EXAMPLE 3

1,3-Diacetyl-2,3,4,6-tetrahydro-2-oxo-1H-thieno[3,4-d]imidazole-4-pentanoic acid [N,N-diacetyldehydrobiotin]

60.7 g. (180 mmol) of N,N'-diacetyldehydrobiotinacetyl anhydride and some N,N'-diacetyldehydrobiotin were dissolved in 85 ml. of methylene chloride followed by 250 ml. of glacial acetic acid. The solution was heated to 35°–40° C. under an inert atmosphere followed by the addition of 6.5 ml. (360 mmol) water. The reaction was continued for 5 hours after the water addition. An additional 3.25 ml. (180 mmole) of water were then added and the reaction was continued 2 more hours. The solvent was then stripped under vacuum leaving crystalline tan product. The product is redissolved in toluene and the solvent is again removed. The product is dried under high vacuum giving 50.5 g. of solids.

25.0 g. of the solids were dissolved in 60 ml. of heated chloroform. This solution was poured onto an 80 ml. silica gel (type 60) column and eluted with ~500 ml. chloroform to yield 24.27 g. of slightly off white solid. The remainder of the product was treated in the same manner yielding a total of 48.89 g. of crude product. Recrystallization from 185 ml. hot methylene chloride/85 ml. hexane gave first crop of 30.33 g. and second crop 10.01 g. (yield 80%). The remaining 20% can be recycled in further recrystallizations.

EXAMPLE 4

1,3-Diacetyl-hexahydro-2-oxo-1H-thieno[3,4-d]imidazole-4-pentanoic acid acetyl anhydride [N,N'-diacetylbiotin acetic anhydride]

In a 50 ml. glass liner was charged 2.5 g. fresh 5% Pd/C. The catalyst was dampened with acetic anhydride. 2.5 g. of N,N'-diacetyldehydrobiotin acetyl anhydride high in 1-isomer were added. The mixture was diluted to 50 ml. with acetic anhydride. The mixture was hydrogenated in a rocker-type autoclave at 450 p.s.i. of $H_2$ at 85° C., for 6 hours. After cooling, the catalyst is centrifuged, washed and recentrifuged. The solutions are stripped and the remaining small amount of Pd/C is filtered through Celite. The solvent was stripped again and 2.27 g. of a colorless oil obtained (yield 91%).

EXAMPLE 5

1,3-Diacetyl-hexahydro-2-oxo-1H-thieno[3,4-d]imidazole-4-pentanoic acid acetyl anhydride [N,N'-diacetylbiotin acetic anhydride]

5.0 g. of damp Raney nickel was weighed out and slurried in 40 ml. methanol. The catalyst was centrifuged and the methanol decanted. The catalyst was reslurried in 40 ml. of distilled acetic anhydride. After centrifugation and decanting of the acetic anhydride, the catalyst was loaded in a 50 ml. glass liner. Then 2.5 g. of N,N'-diacetyldehydrobiotin was charged into the liner and the total volume was brought up to 50 ml. by addition of acetic anhydride.

Hydrogenation was carried out in a rocker-type autoclave at 850 p.s.i. of $H_2$ at 85° C. for 13 hours. After cooling and venting of $H_2$ the solution was decanted through Celite. The catalyst was washed with an additional 50 ml. of acetic anhydride. Stripping of the solvent and high vacuum yielded 2.72 g. of oil (yield 96%).

EXAMPLE 6

The following tables 1 and 2 illustrate the reduction of compounds III and IV to compound V employing typical catalytic species disclosed herein. The tables also illustrate several instances where catalysts can be reused with retention of activity.

Although compounds III and IV are illustrated with some specificity in the Table, is is to be understood that both compounds III and IV can be reduced by any of the catalysts employed and with similar results.

TABLE

| Catalyst | wt (III)/wt (cat.) | | $H_2$ p.s.i. | T °C. | Time/hr. | Solvent | % Reduction |
|---|---|---|---|---|---|---|---|
| Pd $Cl_2$ | 20 | | 500 | 85 | 2 | acetic acid | 100 |
| " | 20 | | 500 | 25 | 4 | methanol | 100 |
| " | 200 | | 500 | 85 | 2 | acetic acid | 25 |
| " | 200 | | 500 | 85 | 2 | acetic anhydride | 58 |
| " | 200 | | 500 | 40 | 10 | acetic anhydride | 62 |
| " | 200 | | 500 | 85 | 2 | acetic anhydride | 30 |
| $Pd_2$ ($\phi$CH=CHC(=O)—CH=CH$\phi$)$_3$ | 200 | | 500 | 85 | 10 | acetic anhydride | 10 |
| $Pd_2Cl_2$ (CH$_3$-C=C-CH$_2$OCH$_3$)$_2$ | | | | | | | |
| Pd (dimethylglyoxime) | 400 | | 850 | 85 | 10 | acetic anhydride | 23 |
| | 400 | | 550 | 85 | 10 | acetic anhydride | 23 |
| $PdCl_2$ (2-aminopyridine-NH$_2$) | | | | | | | |
| Pd $(OH)_2$ | 400 | | 850 | 85 | 10 | acetic anhydride | 36 |
| 20% Pd $(OH)_2$/C | 10 | | 60 | 25 | 2 | acetic anhydride | 100 |
| " | 40 | | 60 | 25 | 2 | acetic anhydride | 53 |
| " | 400 | | 850 | 85 | 10 | acetic anhydride | 40 |
| 5% Pd/C | 20 | | 450 | 85 | 6 | acetic anhydride | 100 |
| 5% Pd/C (1st recycle) | 20 | | 450 | 85 | 6 | acetic anhydride | 93 |
| 5% Pd/C (2nd recycle) | 20 | | 450 | 85 | 6 | acetic anhydride | 95 |
| 5% Pd/C (19th recycle) | 20 | | 550 | 85 | 9 | acetic anhydride | 63 |
| 5% Pd/C (20th recycle) | 20 | | 450 | 85 | 6 | acetic anhydride | 95 |
| 5% Pd(S)/C | 20 | | 460 | 70 | 2 | acetic anhydride | 37 |
| " | 13.3 | | 400 | 50 | 1 | acetic anhydride | 20 |
| 10% Pd/C (3rd recycle) | 10 | | 400 | 50 | 1 | acetic anhydride | 52 |
| Raney nickel | 1.0 | | 1950 | 65 | 4 | acetic acid | >90 |
| " | 0.33 | | 500 | 70 | 10 | acetic anhydride | 84 |
| " | 0.33 | | 500 | 80 | 10 | acetic anhydride | 83 |
| " | 0.33 | (3rd recy.) | 550 | 80 | 13 | acetic anhydride | 70 |
| " | 0.33 | (7th recy.) | 550 | 80 | 13 | acetic anhydride | >10 |
| " | 0.5 | | 850 | 85 | 13 | acetic anhydride | 100 |
| Raney cobalt | 0.36 | | 1870 | 65 | 2 | acetic acid | ~3 |

Table 2

| Catalyst | WtIV*/Wt. Cat. | $H_2$psi | T° C. | Time/hr. | Solvent | % Reduction |
|---|---|---|---|---|---|---|
| 10%Pt/C | 200 | 500 | 85 | 6 | acetic anhydride | 20 |
| $PtO_2$ | 40 | 550 | 85 | 6 | acetic anhydride | 81 |
| $PtO_2$ | 20 | 55 | 25 | 3.5 | methanol | 33 |
| $PtO_2$ | 20 | 300 | 25 | 6 | methylene chloride | 38 |
| 5%Pd/C | 200 | 550 | 85 | 6 | acetic anhydride | 100 |

*($R_1$ = $CH_3$)

EXAMPLE 7

Biotin 2.5 g. of N,N'-diacetylbiotin acetic anhydride d-isomer was mixed with 200 ml. of NaOH solution. This mixture was brought to reflux and maintained for 45 minutes. The oil globules of N,N'-diacetylbiotin acetic anhydride disappear as biotin is formed.

The solution is stripped to ~20 ml. and then acidified with HCl until a pH of 1-2 whereupon a cream white precipitate of biotin falls out. The 1.43 g. obtained represents an 87% recovery.

100 ml. of $H_2O$ were added to the crude biotin. It was boiled with 0.5 g. of Norit SG-SV for 2 hours. The charcoal was filtered. Cooling in refrigeration at ~0° C. yielded white crystalline needles. Filtration and drying gave 0.82 g. $[\alpha]_{25}^D = -89.0$. Pure l-isomer is known to have a rotation of −91.3.

The mother liquor was stripped to 25 ml. and the pH was made slightly acidic with HCl. A further 0.1 g. of biotin was obtained. The mother liquor contained 0.4 g. of biotin.

EXAMPLE 8

1,3-Diacetyl-2,3-dihydro-2-oxo-1H-thieno[3,4-d]imidazole-4-pentanoic acid acetyl anhydride [N,N'-diacetylaromatic biotin acetyl anhydride]

0.5 g. of 2,3-dihydro-2-oxo-1H-thieno[3,4-d]imidazole-4-pentanoic acid (aromatic biotin) were placed in 15 ml. of distilled acetic anhydride. The solution was heated at 110° C. in excess of 2 hours whereupon the product was formed. The anhydride was stripped leaving a quantitative yield of light brown semi-solid product.

EXAMPLE 9

1,3-Diacetyl-hexahydro-2-oxo-1H-thieno[3,4-d]imidazole-4-pentanoic acid acetyl anhydride [N,N'-diacetylbiotin acetic anhydride]

1.45 g. of N,N'-diacetylaromatic biotin acetyl anhydride were dissolved in ~20 ml. acetic anhydride to which about 80 ml. of acetic acid were added. The solution was placed in a glass liner and 4.2 g. of 10% Pd/C were added. The hydrogenation was carried out in a rocking autoclave at 2000 psi $H_2$ at 70° C. for 10 hours. The reaction was cooled and the catalyst was filtered out. The stripping of the acetic acid/anhydride mixture yielded 80%, i.e., 1.16 g. of the oily product.

EXAMPLE 10

Biotin

The following example illustrates the direct hydrogenation of dehydrobiotin to biotin without prior diacylation. Low yields of biotin and desulfurization products are obtained.

0.8 g. of dehydrobiotin was dissolved in 100 ml. glacial acetic acid. 2.4 g. of 10% Pd/C were added. The solution was charged into a glass liner and hydrogenated at 2000 psi H$_2$ at 70° C. for 10 hours. After cooling the reaction, the catalyst was filtered and washed with acetic acid and methanol. The filtrate and washings were combined and stripped yielding ~700 mg. of material. This was mixed with 50 ml. of 1:1 mixture of methanol/ethanol. 90 mg. of biotin crystallized out — 11% yield. The filtrate contained mostly starting material with some desulfurized product and yet slightly more biotin.

EXAMPLE 11 d,l-Biotin

The following example illustrates the direct hydrogenation of aromatic biotin without prior diacylation. Again relatively low yields of biotin and desulfurization products are obtained.

400 mg. of aromatic biotin were added to 50 ml. absolute ethanol. This mixture and 1.2 g. of 5% Pd/C were transferred to a glass liner. Hydrogenation was carried out at 2000 psi H$_2$ at 70° C. for 3 hours. Filtration and washing of catalyst yielded 197 mg. of product. Thin layer chromatography against authentic samples showed the material to be ~30% d,l-biotin and a mixture of ~30% desulfurized product and ~40% aromatic biotin.

EXAMPLE 12

1,3-Diacetyl-2,3,4,6-tetrahydro-2-oxo-1H-thieno[3,4-d]imidazole-4-pentanoic acid methyl ester [N,N'-diacetyldehydrobiotin methyl ester]

25.0 g. of dehydrobiotin in 350 ml. of dry methanol was brought to reflux. Approximately 15 drops of concentrated sulfuric acid were added and the solution was refluxed for 6 hours. The solvent was removed and the products (a mixture of 6a-methoxy-2-oxo-hexahydro-1H-thieno[3,4-d]imidazole-4-pentanoic acid methyl ester and 3a-methoxy-2-oxo-hexahydro-1H-thieno[3,4-d]imidazole-4-pentanoic acid methyl ester) were dissolved in 150 ml. chloroform and washed with 100 ml. saturated NaHCO$_3$ solution. After drying the chloroform with Na$_2$SO$_4$ and its removal, 33.58 g. of the intermediate oily product were isolated. The above crude intermediate was mixed with 200 ml. of distilled anhydride. The solution was heated under an inert atmosphere for 4 hours. Stripping of acetic anhydride yielded a light amber oil. The N,N'-diacetyldehydrobiotin methyl ester was then eluted through a silica plug with methylene chloride. Stripping of the methylene chloride yielded a colorless crystalline product (30.9 g., 88% yield).

EXAMPLE 13

1,3-Diacetyl-hexahydro-2-oxo-1H-thieno[3,4-d]imidazole-4-pentanoic acid methyl ester[N,N'-diacetylbiotin methyl ester]

In a 50 ml liner charged 40.0 mg of 5% Pd/C and a few mls of distilled anhydride under an inert atmosphere. Next 418.0 mg of N,N'-diacetylbiotin methyl ester was added and the mixture was diluted to 50 ml with acetic anhydride. Hydrogenation was carried out at 550 psi of H$_2$, 85° C., for 6 hours. The catalyst was centrifuged and washed with acetic anhydride. The catalyst fines were removed through Celite. Stripping of the anhydride solutions yielded 419.7 mg of pale yellow oil. The yield was quantitative.

EXAMPLE 14

1,3-Diacetyl-hexahydro-2-oxo-1H-thieno[3,4-d]imidazole-4-pentanoic acid methyl ester[N,N'-diacetylbiotin methyl ester]

In a 50 ml glass liner charged 12.8 mg of platinum oxide dampened with acetic anhydride. 417.7 mgs of N,N'-diacetyldehydrobiotin methyl ester high in the 1-isomer were added. The mixture was diluted to 50 ml with acetic anhydride. Hydrogenation was carried out at 550 psi of H$_2$, 85° C., for 6 hours. After cooling the mixture was filtered through Celite removing the Pt metal. Stripping of solvent yielded a colorless oil. Analysis showed ~20% of starting material and 80% of reduction product high in the 1-isomer proportional to that in the starting material.

EXAMPLE 15

1,3-Diacetyl-hexahydro-2-oxo-1H-thieno[3,4-d]imidazole-4-pentanoic acid methyl ester[N,N'-diacetylbiotin methyl ester]

In a 50 ml liner charged 100.0 mg of 5% Pd/C in acetic anhydride. To that was added 500.0 mg of N,N'-diacetyldehydrobiotin methyl ester $[\alpha]_D^{25} = -114.0$. The mixture was hydrogenated in 50 mls of acetic anhydride at 550 psi hydrogen, 85° C., for 6 hours. The mixture was cooled and filtered through Celite which was washed with 15 ml of acetic anhydrige. Stripping gave 503.9 mg of colorless crystalline solid. $[\alpha]_D^{25} = -67.2$. (After hydrolysis there was obtained 88% yield of biotin with $[\alpha]_D^{25} = +80.9$. The rotation is lower than that of pure $[\alpha]_D^{25} = +91.3$ because of presence of epi-biotin which has the opposite rotation and can be removed easily by crystallization. Final biotin yield is 80%).

EXAMPLE 16

1,3-Diacetyl-hexahydro-2-oxo-1H-thieno[3,4-d]imidazole-4-pentanoic acid methyl ester[N,N'-diacetyl biotin methyl ester]

To 1 ml of trifluoroaceticanhydride was added 10 ml of trifluoroacetic acid which was mixed with 4 ml. of HSi(CH$_2$CH$_3$)$_3$.

The reaction was allowed to stand for one half hour, followed by the addition of 1.0 g of N,N'-diacetyldehydrobiotin methyl ester. The solution was heated at 80° C. for about 24 hours. The reaction was stripped to a mixture of two phases, which was extracted with chloroform affording a semi-crystalline material. Yield ~100%. Analysis showed ~6/1 ratio of all-cis/epi biotin.

I claim:

1. A compound of the formula

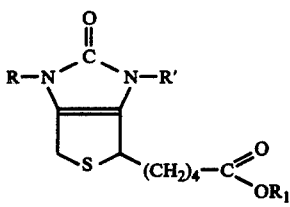

III wherein R and R' are lower alkanoyl; and $R_1$ is hydrogen, lower alkyl or lower alkanoyl.

2. The compound of claim 1 wherein said compound is

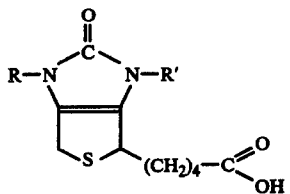

IV wherein R and R' are lower alkanoyl.

3. The compound of claim 1 wherein said compound is

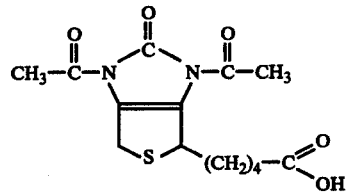

IV-a

4. The compound of claim 1 wherein said compound is

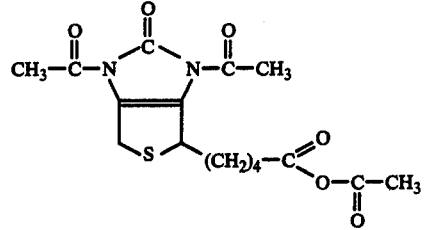

IIIa

5. The compound of claim 1 wherein said compound is

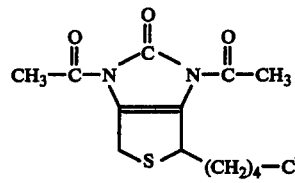

6. A compound of the formula

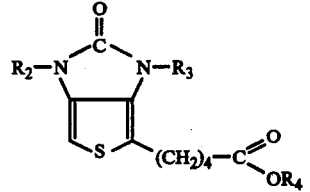

VIII wherein $R_2$ and $R_3$ are lower alkanoyl and $R_4$ is hydrogen, lower alkyl or lower alkanoyl.

7. The compound of claim 6 wherein said compound is

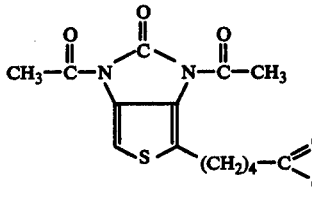

* * * * *